United States Patent
Hamelers et al.

(10) Patent No.: US 8,431,368 B2
(45) Date of Patent: Apr. 30, 2013

(54) METHOD FOR THE ENZYMATIC PRODUCTION OF FATTY ALCOHOL AND/OR FATTY ACID

(75) Inventors: Hubertus Victor M. Hamelers, Heelsum (NL); Kirsten Johanna J. Steinbusch, Wageningen (NL); Cees Jan Nico Buisman, Harich (NL)

(73) Assignee: Waste2Chemical Knowledge B.V. (NL)

( * ) Notice: Subject to any disclaimer, the term of this patent is extended or adjusted under 35 U.S.C. 154(b) by 1 day.

(21) Appl. No.: 12/745,226

(22) PCT Filed: Dec. 16, 2008

(86) PCT No.: PCT/EP2008/010878
§ 371 (c)(1),
(2), (4) Date: Aug. 26, 2010

(87) PCT Pub. No.: WO2009/083174
PCT Pub. Date: Jul. 9, 2009

(65) Prior Publication Data
US 2010/0317071 A1 Dec. 16, 2010

(30) Foreign Application Priority Data
Dec. 27, 2007 (EP) .................... 07076132

(51) Int. Cl.
*C12P 7/64* (2006.01)
*C12P 9/00* (2006.01)

(52) U.S. Cl.
USPC .......................................... 435/134; 435/131

(58) Field of Classification Search .................. 435/131, 435/134
See application file for complete search history.

(56) References Cited

FOREIGN PATENT DOCUMENTS
WO 2007136762 11/2007
WO WO 2007/136762 A2 * 11/2007

OTHER PUBLICATIONS

Barker et al., "The Synthesis of Butyric and Caproic Acids from Ethanol and Acetic Acid by *Clostridium kluyveri*" Proceedings of the National Academy of Sciences vol. 31, No. 12 (1945). pp. 373-381.
Chan et al., "Conversion of Municipal Solid Wastes to Carboxylic Acids by Thermophilic Fermentation" Applied Biochemistry and Biotechnology—Part A Enxyme Engineering and Biotechnology (2003) 111(2). pp. 93-112.
Database WPI Week 199538. Thompson Scientific, London XP002512350. (1995) abstract.
Database WPI Week 199641. Thompson Scientific, London XP002482110. (1996) abstract.
Holtzapple et al., "Biomass Conversion to Mixed Alcohol Fuels Using the MixAlco Process." ACS Symposium Series (1997) 666: pp. 130-142.
Levy et al., "Biorefining of Biomass to Liquid Fuels and Organic-Chemicals" Enzyme Microb. Tech (1981) pp. 207-215.
Seedorf et al., "The genome of *Clostridium kluyveri*, a strict anaerobe with unique metabolic features" Proceedings of the National Academy of Sciences in the United Sates of America (2008) 105(6): pp. 2128-2133.
Simon et al., "Reduction of 2-Enoates and Alkanoates with Carbon Monoxide or Formate, Viologens, and *Clostridium thermoaceticum* to Saturated Acids and Unsaturated and Saturated Alcohols" Angewandte Chemie International Edition in English, vol. 26, No. 8 (1987) XP002512412. pp. 785-787.
Stadtman et al., "Fatty acid synthesis by enzyme preparations of *Clostridium kluyveri*" Journal of Biological Chemistry. (1949) 184(2): pp. 769-793.
Steinbush et al., "Alcohol production through volatile fatty acid reduction with hydrogen as electron donor by mixed cultures" Water Research vol. 42, No. 15 (2008) pp. 4059-4066.

* cited by examiner

*Primary Examiner* — Karen Cochrane Carlson
*Assistant Examiner* — Natalie Moss
(74) *Attorney, Agent, or Firm* — Bozicevic Field & Francis LLP; Bret E. Field

(57) ABSTRACT

The invention relates to a method for the enzymatic production of $C_6$-$C_{18}$ fatty alcohol and/or $C_8$-$C_{18}$ fatty acid, by carbon chain elongation, comprising the steps of: i) providing organic $C_2$-$C_6$ compounds; ii) subjecting the organic $C_2$-$C_6$ compounds to enzymatic carbon chain elongation in the presence of an electron donor; and iii) separating the formed $C_6$-$C_{18}$ fatty alcohol and/or $C_8$-$C_{18}$ fatty acid.

18 Claims, No Drawings

METHOD FOR THE ENZYMATIC PRODUCTION OF FATTY ALCOHOL AND/OR FATTY ACID

The present invention relates to a method for the enzymatic production of fatty alcohol and/or fatty acids, to a method for covalently coupling carbonic acids obtained in the enzymatic production method, to a method for providing biofuel wherein the enzymatic production method is used, and finally to the use of fatty acids in the production of biofuel.

In view of global climate changes due to carbon dioxide emission, the limited resources for fuel and the desire to be less dependent on oil and gas producing parties, there is an increased need for biofuel. Biomass may be a starting material for the production of chemicals and (bio)fuel. Massive production may have a negative effect on carbon dioxide emission, food production, biodiversity, environment, and the like. In view of these possible negative effects an EU directive indicates that biomass to be used for (bio)fuel is to be produced in an environmentally acceptable manner. Biofuel may be produced starting from wood based/or wood like biomass not suitable for food or food production.

Accordingly, this biomass will not compete with food production. Wood base or wood like biomass comprises lignocelllulose which is a combination of lignine and hemicelluloses. At present biomass may be converted in long chain hydrocarbons by several processes. Examples are biomass gasification in combination with Fisher-Tropsch synthesis or by hydrothermal upgrading.

Biomass gasification in combination with Fisher-Tropsch synthesis for the production of biofuel requires from an economic perspective a large scale production resulting in high investment costs and complex and expensive logistics in the provision of biomass to be used.

Hydrothermal upgrading uses wet biomass to be converted in biofuel. Biomass in water at high temperatures (300-360° C.) and at high pressure (100-180 bar) is converted in crude. Oxygen is removed in the form of carbon dioxide providing a biocrude product comprising a low oxygen content (10-18 wt %) and a relatively high combustion value (30-35 MJ/kg).

A biological method comprises a complex conversion of lignocelluloses by micro-organisms into ethanol and/or butanol. These products may be used as fuel. However, due to the short carbon chain and the high polarity they are not appropriate for addition to biodiesel.

The present invention has for its object to provide a method for the enzymatic production of fatty alcohol and/or fatty acid which could be used as such as valuable chemical or could be converted into biofuel. This method makes use of biomass which is not competing with food or food production and is in line with the above mentioned EU directive.

Accordingly, the present invention provides a method for the enzymatic production of $C_6$-$C_{18}$ fatty alcohol and/or $C_8$-$C_{18}$ fatty acid, by carbon chain elongation, comprising the steps of:
 i) providing organic $C_2$-$C_6$ compounds;
 ii) subjecting the organic $C_2$-$C_6$ compounds to enzymatic carbon chain elongation in the presence of an electron donor; and
 iii) separating the formed $C_6$-$C_{18}$ fatty alcohol and/or $C_8$-$C_{18}$ fatty acid.

The present invention is based on the insight that organic $C_2$-$C_6$ compounds could be subjected to an enzymatic carbon chain elongation thereby providing organic compounds with an extended carbon chain. This carbon chain elongation is an enzymatic process which could be carried out by micro-organisms. This enzymatic carbon chain elongation requires the presence of an electron donor. The organic $C_2$-$C_6$ compounds are enzymatically reacting with one another thereby forming organic compounds having an elongated carbon chain. Formed are valuable organic compounds namely $C_6$-$C_{18}$ fatty alcohol and/or $C_8$-$C_{18}$ fatty acid. Not bound by any theory or hypothesis, it is considered that the carbon chain elongation increases by at least two carbon atoms or by more carbon atoms when in the elongation step $C_3$-$C_6$ organic compounds are involved and/or a dimerization or oligomerization takes place.

At this point it is noted that throughout the description the fatty acid may be referred to as a fatty acid or as its protonated form. Accordingly, acetic acid and acetate will refer to the same type of compound unless specifically indicated. Accordingly, the term acetic acid and acetate may be used interchangeably.

The starting organic $C_2$-$C_6$ compounds may be any suitable organic compound. However, the enzymatic carbon chain elongation proceeds effectively and at a better yield when the organic $C_2$-$C_6$ compounds comprise organic $C_2$-$C_6$ carbon acids and/or $C_2$-$C_6$ alcohols. Specific examples of suitable organic $C_2$-$C_6$ compounds are acetate, n-propionate, i-propionate, n-butyrate, i-butyrate, succinate, n-valerate, i-valerate, n-caproate, i-caproate, n-butanol, and i-butanol. Best results (considering yield and/or conversion rate) are obtained with acetate, n-propionate, i-propionate, n-butyrate, ethanol and/or n-butanol.

Any source for organic $C_2$-$C_6$ compounds is suitable for use in the enzymatic carbon chain elongation according to the present invention. Biomass as such may be used. However, it is preferred to use pretreated biomass in which the pretreatment resulted in a release or an improved availability for the enzymatic reaction of the required organic $C_2$-$C_6$ compounds. Such pretreatments may comprise fermentation or other enzymatic reaction and a treatment of biomass (such as wood) with super critical water. Obviously, any carbon source comprising fat, protein, carbohydrate and/or mixtures thereof is in essence suitable provided that directly or by chemical treatment organic $C_2$-$C_6$ compounds are released or made available. Furthermore, it is possible that the pretreatment comprises a mechanical or physical treatment. A mechanical treatment comprises milling, grinding, pressing and the like. Physical pretreatments comprise an exposure to heat, water, steam and the like. Accordingly, there is a preference for using pretreated biomass, fermented biomass or fractions thereof.

As indicated here and before, the enzymatic carbon chain elongation proceeds with the required presence of an electron donor. Accordingly, any inorganic or organic compound which could provide electrons for the carbon chain elongation during the enzymatic conversion is suitable, provided that the electron donor has no negative effect on the enzymatic reaction. In essence, any organic compound which can be used as a metabolic energy source for providing electrons may be used.

In general are suitable on the one hand inorganic compounds such as hydrogen, formate and carbon monoxide. On the other hand are suitable organic $C_1$-$C_6$ compounds having a degree of reduction higher than 4. The degree of reduction indicates the capacity of a compound to reduce other compounds. It is expressed in number of electrons that are involved in the half reaction of the compound with the compounds in the reference oxidation state. Compounds in the reference oxidation state are $HCO_3^-$, $NO_2^-$, $SO_4^-$, water and protons; and have by definition a degree of reduction zero.

The degree of reduction is the amount of electrons involved in this oxidizing half reaction per carbon atom of the compound (see McCarty, P. L., ed. Energetics of organic matter degradation. Water pollution microbiology, ed. R. Mitchell. Vol. 2. 1972, John Wiley & Sons: New York. 91-118). Thus the degree of reduction higher than 4 means that at least 4 electrons are involved in the half reaction of the electron donor.

In case of organic $C_2$-$C_6$ compounds the degree of reduction divided by four gives the moles of $O_2$ needed per C-atom in the organic compound needed for full oxidation to CO2 and H2O. The degree of reduction is maximally 8 for methane.

Suitable electron donors are ethanol, formate, carbon monoxide, methanol, glycerol, lactate, 1,3-dipropanol acetate, n-propionate, i-propionate, n-butyrate, i-butyrate, succinate, n-valerate, i-valerate, n-caproate, i-caproate, n-butanol, i-butanol. Preferred are as an electron donor hydrogen, ethanol, n-butanol and/or mixtures thereof.

The enzymatic reaction may be carried out using enzymes and/or enzyme mixtures and/or enzyme complexes. Practically is the use in this enzymatic reaction of microorganisms. These microorganisms should be suitable for carrying out the carbon chain elongation under reductive anaerobic conditions. The reductive anaerobic conditions takes place at a redox potential (measured against a standard hydrogen electrode) lower than −350 mV, preferably lower than −400 mV, more preferably lower than −450 mV. A suitable range for the redox potential is −350 to −700 mV, such as −400 to −600 mV, such as −450 to −550 mV. Micro organisms suitable for the enzymatic carbon chain elongation under reductive anaerobic conditions may be found in anaerobic sewage sludge or in the sludge of a reactor fermenting acetate and/or ethanol (or other organic $C_2$-$C_6$ compounds). Accordingly, the microorganisms may originate from an inoculum of such anaerobic sewage sludge or reactor. However, other sources of microorganisms may be used. For example, sources for fermentive bacteria, such as clostridia.

When using an inoculum comprising a variety of microorganisms, then it is preferred to inhibit parallel enzymatic reactions, such as the formation of methane. Accordingly, it is preferred that during the enzymatic carbon chain elongation methane formation is substantially inhibited. According to one embodiment the methane formation is suppressed or even inhibited by carrying out a heat pre-treatment. Other pre-treatments comprise carrying out the method at relatively low (acidic) pH. Subjecting the inoculum to an acid treatment. Finally, another option comprises the removal from the reaction system any present carbon dioxide. An alternative or concomitant treatment comprises the addition of a methane formation inhibiting agent. An example of such methane formation inhibiting agent is 2-bromo-ethanosulfonic acid.

The method according to the invention provides in an elegant manner, starting from organic $C_2$-$C_6$ compounds in the provision of $C_6$-$C_{18}$ fatty alcohols and/or $C_8$-$C_{18}$ fatty acids. Preferred from an enzymatic point of view are $C_6$-$C_{18}$ fatty alcohols and $C_8$-$C_{10}$ fatty acids. A preferred produced fatty alcohol is n-hexanol. A preferred fatty acid is n-caprylate. Due to the relatively large carbon chain, are the formed $C_6$-$C_{18}$ fatty alcohols slightly or insoluble in the aqueous medium in which the enzymatic carbon chain elongation is carried out. Accordingly, the produced fatty alcohol and/or fatty acid may be relatively easily separated from the aqueous medium. Suitable separation procedures comprise extraction, precipitation, flotation, sedimentation and/or absorption. Preferred separation procedures comprise solvent extraction. However, phase separation using for instance selective membranes is an alternative possible solution. Obviously, in view of a particular produced $C_6$-$C_{18}$ fatty alcohols and/or $C_8$-$C_{18}$ fatty acid the skilled person may select by routine experimentation the best suitable separation procedure under the residing circumstances.

In general is the pH during the enzymatic production accordingly to the invention maintained between 4-8. However, it is preferred to maintain the pH within the range of 4-6 or more preferably within the range of 5-6. The pH may also be chosen dependent on the various steps of the method for the enzymatic production. Accordingly, the pH may be neutral during the enzymatic carbon chain elongation. A suitable pH may be within the range of 6-8, more preferably a pH in the range of 6.5-7.5, such as pH 7. The separation of the fatty alcohol and/or fatty acid according to the invention may however take place at a relatively acidic pH, such as at a pH of 4-7, more preferably a pH of 4-6, such as a pH of 5-6. Obviously, the skilled person may select the separation pH even in dependence of the intended separation of the $C_6$-$C_{18}$ fatty alcohols and/or $C_8$-$C_{18}$ fatty acid. Even the pH may be selected dependent on a longer or shorter fatty acid or fatty alcohol produced.

The enzymatic method according to the present invention may be carried out continuously or batch wise, such as fed batch wise. Batch wise production has the advantage of having the option of adjusting the temperature and pH in relation to the stage of the method. Furthermore, is provided the possibility of carrying out the pre-treatment of the biomass and/or the inoculums whenever required.

Another aspect of the present invention relates to a process for covalently coupling carbonic acids. In this method carbonic acids are coupled via a so called ketonic decarboxylation. Subject of this ketonic decarboxylation are $C_8$-$C_{18}$ fatty acids produced in the enzymatic carbon chain elongation according to the present invention. It has been confirmed that in particular the $C_8$-$C_{18}$ fatty acids, especially the $C_8$-$C_{10}$ fatty acids, such as n-caprylate, are very effective in this ketonic decarboxylation.

Several known ketonic decarboxylations may be used. A first example is the process disclosed in JP 8198796. This process comprises a reaction of carbonic acids in the vapor phase in the presence of a MgO or CaO catalyst. The reaction temperature is about 250° C. when using the MgO catalyst or about 450° C. using the CaO catalyst. Another exemplified process comprises the dry distillation of the calcium salt of the carbonic acid. In an improved procedure superheated steam is applied. After the addition of a base free carboxylic acid is formed and the calcium salt precipitated and available for recycling into the process. For a micro review see Renz, M., *Ketonization of carboxylic acids by decarboxylation: Mechanism and scope*. European Journal Of Organic Chemistry, 2005 (6): p. 979-988.

Obviously, the skilled person may select any suitable ketonic decarboxylation process. Essential is the use of the $C_8$-$C_{18}$ fatty acids formed in the enzymatic carbon chain elongation reaction according to the invention.

A further aspect of the present invention relates to a method for providing biofuel. Presently, biomass, such as sugar cane is separated by mechanical pre-treatment in a liquid fraction which by fermentation provides ethanol. The ethanol is removed from the aqueous medium by distillation. The energy for the distillation is provided by burning the solid fraction obtained during the mechanical treatment of the sugarcane. The present invention provides an improved method for providing biofuel which overcomes the drawback of the energy requirement for the separation of valuable organic compounds, such as ethanol from the aqueous fermentation medium. The present invention is based on the insight that the ethanol produced during the fermentation as such or after concentration may be used as the electron donor in the process according to the present invention of the enzymatic carbon chain elongation. The produced $C_6$-$C_{18}$ fatty alcohol and/or $C_8$-$C_{18}$ fatty alcohol as such may be used as biofuel or after a subsequent chain elongation such as by ketonic decarboxylation. Accordingly, the present invention provides a method for providing biofuel, comprising the steps of:

i) treating biomass to provide a carbohydrate comprising fraction;
ii) fermenting the carbohydrate comprising fraction to ethanol;
iii) fermenting the treated biomass so as to provide organic $C_2$-$C_6$ compounds; and
iv) subjecting the $C_2$-$C_6$ compounds to carbon chain elongation according to the claims 1-18 using at least ethanol of step ii) as the organic electron donor.

Finally, the present invention relates to the use of $C_8$-$C_{18}$ fatty acids, in particular caprylic acid in the production of biofuel.

The following examples are given as an illustration of the various methods according to the invention but are not intended to limit the methods according to the invention to any extent.

EXAMPLE 1

An inoculum was obtained from anaerobic sewage sludge. Fermentation vials with a volume of 125 ml were filled with 37.5 ml medium. The medium per liter:

|  | Amount or Volume |
|---|---|
| Substrate | 50 mM |
| $(NH_4)H_2PO_4$ | 3600 mg |
| $MgCl_2 \cdot 6H_2O$ | 500 mg |
| $CaCl_2 \cdot 2H_2O$ | 200 mg |
| KCl | 500 mg |
| trace metals[1] | 1 ml |
| B-vitamins[2] | 1 ml |

[1] Pfennig trace metals solution in 100 ml
[2] B-vitamins solution in 100 ml

|  | Weight in mg |
|---|---|
| $ZnSO_4 \cdot 7H_2O$ | 100.0 |
| $MnCl_2 \cdot 4H_2O$ | 30.0 |
| $H_3BO_3$ | 300.0 |
| $CoCl_2 \cdot 6H_2O$ | 200.0 |
| $CuCl_2 \cdot H_2O$ | 10.0 |
| $NiCl_2 \cdot 6H_2O$ | 20.0 |
| $Na_2MoO_4 \cdot 7H_2O$ | 30.0 |
| $FeCl_2 \cdot 4H_2O$ | 1500.0 |
| $AlCl2 \cdot 6H2O$ | 45.0 |
| $Na_2SeO_3$ | 10.0 |

| B-vitamins | Weight in mg |
|---|---|
| Biotin | 106 |
| Folic acid | 5 |
| pyridoxal-HCl | 2.5 |
| Lipoic acid | 270 |
| Riboflavin | 13 |
| Thiamine-HCl | 13 |
| Ca-D-pantothenate | 414 |
| Cyanocobalamin | 13 |
| P-aminobenzoic acid | 11 |
| Nicotinic acid | 15 |

The medium was prepared as described by Phillips, J. R., et al., *Biological production of ethanol from coal synthesis gas-medium development studies*. Applied Biochemistry and Biotechnology, 1993. 39: p. 559-571. 50 mM acetate is added and further 2-bromo-ethanosulfonic acid. The pH of the medium was adjusted to 5.5 and the fermentation vials were closed using a rubber stopper. The gas phase in the fermentation bottles consisted of nitrogen. An inoculum originated from an anaerobic reactor is used for the conversion of acetate and ethanol. The vials are incubated at 30° C. and agitated at 200 rpm. Over a time period of 99 days was the pH measured and adjusted to a pH of 5.35-5.65 using hydrochloric acid or sodium hydroxide.

EXAMPLE 2

Same conditions as in example 1 have been used but instead of 50 mM acetate 50 mM ethanol was added to the medium. Furthermore, the gas phase comprised a mixture of nitrogen and hydrogen at a partial hydrogen pressure of 1.5 bar.

EXAMPLE 3

In comparison to example 2 was added to the medium 50 mM acetate and 50 mM ethanol.

The results of the examples 1, 2 and 3 are summarized in the following table

TABLE average concentration of the consumed substrate (negative value) and fermentation products (positive values) after 99 days; each experiment was carried out in triplo

| | Substrate | | |
|---|---|---|---|
| System conditions | Example 1 | Example 2 | Example 3 |
| Products (mg/l) | | | |
| Ethanol | 13.3 ± 2.6 | −1879 ± 30 | −1458 ± 255 |
| Propanol | 0.4 ± 0.9 | 5.7 ± 2.9 | 7.7 ± 0.4 |
| n-Butanol | 23.9 ± 3.9 | 122 ± 59 | 32.0 ± 8.3 |
| n-Hexanol | 6.8 ± 1.8 | 22.3 ± 6.6 | 84.1 ± 22.1 |
| Acetate | −1841 ± 152 | −2635 ± 31 | −14.9 ± 12.7 |
| Propionate | 31.1 ± 4.6 | 51.1 ± 5.8 | 18.7 ± 9.9 |
| i-Butyrate | 61.7 ± 39.7 | 596 ± 45 | 33.7 ± 23.1 |
| n-Butyrate | 415.6 ± 21.7 | 1485 ± 92.3 | 164 ± 77.2 |
| i-Valerate | 29.1 ± 2.0 | 30.7 ± 6.5 | 26.0 ± 3.2 |
| n-Valerate | 12.8 ± 1.1 | 13.0 ± 1.3 | 5.5 ± 0.5 |
| n-Carpoate | 323 ± 25 | 667.5 ± 37.1 | 159 ± 9.3 |
| n-Caprylate | 512 ± 111 | 649.2 ± 93.5 | 605 ± 46 |
| C recovery (%) | 110.3 ± 6.9 | 105.1 ± 8.6 | 96.4 ± 9.0 |
| E recovery (%) | 105.0 ± 6.6 | 102.3 ± 7.8 | 92.4 ± 17.4 |

The invention claimed is:

1. A method for the enzymatic production of C6-C18 fatty alcohol and/or C8-C18 fatty acid, by carbon chain elongation, comprising the steps of:

i) providing organic C2-C6 compounds;
ii) subjecting the organic C2-C6 compounds to enzymatic carbon chain elongation in the presence of an electron donor; and
iii) separating the formed C6-C18 fatty alcohol and/or C8-C18 fatty acid, wherein the enzymatic carbon chain elongation is carried out by microorganisms found in anaerobic sewage sludge.

2. The method according to claim 1, wherein the organic $C_2$-$C_6$ compounds comprise organic $C_2$-$C_6$ carbon acids and/or $C_2$-$C_6$ alcohols.

3. The method according to claim 1 or 2, wherein the organic $C_2$-$C_6$ compounds comprise acetate, n-propionate, i-propionate, n-butyrate, i-butyrate, succinate, n-valerate, i-valerate, n-caproate, i-caproate, n-butanol, and i-butanol.

4. The method according to claim 3, wherein the organic $C_2$-$C_6$ compounds comprise acetate, n-propionate, i-propionate, n-butyrate, ethanol and/or n-butanol.

5. The method according to claim 1, wherein the organic $C_2$-$C_6$ compounds are provided in the form of biomass, pretreated biomass, fermented biomass and/or fractions thereof.

6. The method according to claim 1, wherein the electron donor is selected from the group comprising hydrogen, formate, carbon monoxide, organic $C_1$-$C_6$ compounds with a degree of reduction higher than 4 and/or mixtures of the electron donors.

7. The method according to claim 6, wherein the electron donor is hydrogen, ethanol, n-butanol and/or mixtures thereof.

8. The method according to claim 1, wherein the enzymatic carbon chain elongation is carried out by microorganisms under reductive anaerobic conditions at a redox potential lower than −350 mV.

9. The method according to claim 8, wherein the microorganisms originate from an inoculum from anaerobic sewage sludge.

10. The method according to claim 9, wherein the microorganisms are a fermentive bacteria.

11. The method according to claim 1, wherein the produced $C_6$-$C_{18}$ fatty alcohol is $C_6$-$C_8$ fatty alcohol, and/or the produced $C_8$-$C_{18}$ fatty acid is $C_8$-$C_{10}$ fatty acid.

12. The method according to claim 1, wherein the $C_6$-$C_{18}$ fatty alcohol and/or $C_8$-$C_{18}$ fatty acid are separated by extraction, precipitation, flotation, sedimentation and/or absorption.

13. The method according to claim 8, wherein during the enzymatic carbon chain elongation methane formation is substantially inhibited.

14. The method according to claim 13, comprising a heat pretreatment.

15. The method according to claim 13, comprising the addition of a methane formation inhibiting agent.

16. The method according to claim 1, wherein the pH is maintained between 4-8.

17. The method according to claim 16, wherein the separation of the $C_6$-$C_8$ fatty alcohol and/or $C_8$-$C_{18}$ fatty acid is carried out at pH 4-7.

18. The method as claimed in claim 16, wherein the enzymatic carbon chain elongation is carried out at pH 6-8.

* * * * *